(12) United States Patent
Kahya et al.

(10) Patent No.: US 12,029,504 B2
(45) Date of Patent: *Jul. 9, 2024

(54) ELECTROMAGNETIC NAVIGATION DEVICE FOR GUIDING AND TRACKING AN INTERVENTIONAL TOOL

(71) Applicant: KONINKLIJKE PHILIPS N.V., Eindhoven (NL)

(72) Inventors: Neriman Nicoletta Kahya, Eindhoven (NL); Molly Lara Flexman, Melrose, MA (US); David Paul Noonan, New York, NY (US); Aryeh Leib Reinstein, Bronx, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 190 days.

This patent is subject to a terminal disclaimer.

(21) Appl. No.: 17/581,122

(22) Filed: Jan. 21, 2022

(65) Prior Publication Data
US 2022/0142716 A1 May 12, 2022

Related U.S. Application Data

(63) Continuation of application No. 15/764,094, filed as application No. PCT/IB2016/055682 on Sep. 23, 2016, now Pat. No. 11,259,877.

(Continued)

(51) Int. Cl.
A61B 34/20 (2016.01)
A61B 5/00 (2006.01)
(Continued)

(52) U.S. Cl.
CPC ............... A61B 34/20 (2016.02); A61B 5/06 (2013.01); A61B 5/062 (2013.01); A61B 5/066 (2013.01);
(Continued)

(58) Field of Classification Search
CPC ........... A61B 34/20; A61B 5/06; A61B 5/062; A61B 5/066; A61B 5/6851; A61B 6/487;
(Continued)

(56) References Cited

U.S. PATENT DOCUMENTS 11,259,877 B2 * 3/2022 Kahya .................. A61B 5/6851
2006/0063973 A1 3/2006 Makower
(Continued)

FOREIGN PATENT DOCUMENTS

AU 2006202149 B2 6/2006
EP 2517665 A1 10/2012
(Continued)

*Primary Examiner* — Joel Lamprecht

(57) ABSTRACT

An electromagnetic navigation device for guiding and tracking an interventional tool (40) within an anatomical region. The electromagnetic navigation device employs a guidewire (20) insertable into the anatomical region, and a hub (30) translatable and/or rotatable in conjunction with the interventional tool (40) relative to the guidewire (20). In operation, the guidewire (20) includes one or more guidance electromagnetic sensors generating guidance data informative of an electromagnetic sensing of a position and/or an orientation of the guidewire (20) relative to the anatomical region, and the hub (30) includes a tracking electromagnetic sensor (31) generating tracking data informative of an electromagnetic sensing of a position and/or an orientation of the hub (30) relative to the guidewire (20). Responsive to the electromagnetic sensing data, a navigation controller (76) controls a determination of a position and/or an orientation of the interventional tool (40) relative to the guidewire (20).

20 Claims, 8 Drawing Sheets

Related U.S. Application Data

(60) Provisional application No. 62/236,192, filed on Oct. 2, 2015.

(51) Int. Cl.
*A61B 5/06* (2006.01)
*A61B 6/00* (2006.01)
*A61B 6/12* (2006.01)
*A61B 90/00* (2016.01)
*A61M 25/01* (2006.01)
*A61M 25/09* (2006.01)

(52) U.S. Cl.
CPC .............. *A61B 5/6851* (2013.01); *A61B 6/12* (2013.01); *A61B 6/487* (2013.01); *A61B 2034/2051* (2016.02); *A61B 2090/376* (2016.02); *A61B 2562/043* (2013.01); *A61M 25/0127* (2013.01); *A61M 25/09* (2013.01)

(58) Field of Classification Search
CPC .............. A61B 6/12; A61B 2562/043; A61B 2034/2051; A61B 2090/376; A61M 25/09; A61M 25/0127
See application file for complete search history.

(56) References Cited

U.S. PATENT DOCUMENTS

| | | |
|---|---|---|
| 2007/0208252 A1 | 9/2007 | Makower |
| 2008/0125846 A1 | 5/2008 | Battle |
| 2008/0262473 A1 | 10/2008 | Kornblau |
| 2009/0062739 A1 | 3/2009 | Anderson |
| 2013/0131503 A1 | 5/2013 | Schneider |

FOREIGN PATENT DOCUMENTS

| | | |
|---|---|---|
| EP | 2517677 A1 | 10/2012 |
| WO | 2013028937 A1 | 2/2013 |

\* cited by examiner

ELECTROMAGNETIC NAVIGATION DEVICE FOR GUIDING AND TRACKING AN INTERVENTIONAL TOOL

CROSS-REFERENCE TO PRIOR APPLICATIONS

This application is a Continuation of U.S. Ser. No. 15/764,094, filed Mar. 28, 2018 which is the U.S. National Phase application under 35 U.S.C. § 371 of International Application No. PCT/IB2016/055682, filed on Sep. 23, 2016, which claims the benefit of U.S. Provisional Patent Application No. 62/236,192, filed on Oct. 2, 2015. These applications are hereby incorporated by reference herein.

FIELD OF THE INVENTION

The present disclosure generally relates to guiding and tracking an interventional tool (e.g., a catheter, a stent deployment system, a sheath, etc.) within an anatomical region (e.g., a cephalic region, a cervical region, a thoracic region, an abdominal region, a pelvic region, etc.). The present disclosure specifically relates to a novel and inventive guidewire and hub including electromagnetic sensors for guiding and tracking the interventional tool within the anatomical region by electromagnetically sensing a position and/or an orientation of the interventional tool within the anatomical region.

BACKGROUND OF THE INVENTION

Endovascular aneurysm repair ("EVAR") has replaced open surgery as the most common technique for the repair of abdominal aortic aneurysms ("AAA"). An EVAR procedure is typically carried out under x-ray fluoroscopy guidance and uses significant amounts of contrast and radiation to position and deploy the stent graft correctly.

The most common complication from EVAR is endoleaks resulting from an insufficient seal of the stent graft to the aorta. Endoleaks involve incorrect flow around the stent, such as, for example, flow around the stent at the proximal or distal attachment site, flow through the graft wall and retrograde flow from the branches.

Another complication around EVAR involves ischemia of the aortic side branches (e.g., colonic, renal, and pelvic arteries). This ischemia can occur due to misplacement of the stent graft such that the stent partially or completely covers one of the side vessels and is associated with a lack of high-quality imaging technology as well as the learning curve of the endovascular team.

More particularly, in EVAR, stent grafts are contained within a stent-deployment system that is used to navigate the stent to the correct part of the vasculature. The deployment systems tend to be relatively large and stiff endovascular devices. They typically involve a handle or set of knobs and dials at the proximal end to control the various steps around the stent deployment. The stent lies within the distal part of the device and is only released once the device has been navigated to the appropriate location. In some cases the stent completely deploys in one step, while in other cases the stent can be partially deployed to allow for correct positioning and orientation before the final deployment step firmly attaches the stent to the vasculature, typically through the retaining/sealing ring.

The endovascular stent graft requires a sufficient amount of healthy vasculature where it can land its sealing ring. If this is not possible beneath the renal arteries, then the stent will cover those arteries, and must create some alternative way of maintaining flow to those vessels. This can be done with a fenestrated stent (i.e. a stent with windows for the side-branches) in a procedure known as fenestrated endovascular aneurysm repair ("FEVAR") whereby the stent has fenestrations that must be lined up correctly with the side branches and additional stents are placed to connect the side vessels to the main stent.

Concurrently with or alternatively to x-ray guidance, the stent-deployment system may be enabled with electromagnetic ("EM") tracking by embedding a sensor (e.g., a coil) within the system. More particular, EM tracking involves the use of an EM field generator to create a magnetic field in the region of interest. When the sensor is placed within the magnetic field, a current is induced by the sensor whereby the current may be utilized to calculate the position of the sensor relative to the EM generator.

EM sensors may be incorporated into catheters, stent-deployment systems, sheaths and other interventional tools, and are typically integrated at the tip of an interventional tool since that is the most important position for navigation. However, this typically requires redesigning the mechanical properties of the interventional tool to embed the EM sensor as well as an additional lumen to connect the EM sensor to the measurement system at the proximal part of the device. In the case of therapeutic devices, this can limit the use of EM-tracking due to the high burden to re-design, re-verify, and release new interventional tools with EM-tracking integrated.

SUMMARY OF THE INVENTION

The present disclosure provides inventions comprising guidewires and hubs including electromagnetic sensors for guiding and tracking interventional tool (e.g., a catheter, a stent deployment system, a sheath, etc.) within an anatomical region (e.g., a cephalic region, a cervical region, a thoracic region, an abdominal region, a pelvic region, etc.) by electromagnetically sensing a position and/or an orientation of the interventional tool within the anatomical region.

One form of the inventions of the present disclosure is an electromagnetic navigation device for guiding and tracking an interventional tool within an anatomical region. The electromagnetic navigation device employs a guidewire insertable into the anatomical region, and a hub translatable and/or rotatable in conjunction with the interventional tool relative to the guidewire.

In operation, the guidewire includes one or more guidance electromagnetic sensors generating guidance data informative of an electromagnetic sensing of a position and/or an orientation of the guidewire within the anatomical region, and the hub includes a tracking electromagnetic sensor generating tracking data informative of an electromagnetic sensing of a position and/or an orientation of the hub relative to the guidewire.

Collectively, the guidance data and the tracking data are informative of and electromagnetic sensing of a position and/or an orientation of the interventional tool relative to the guidewire.

A second form of the inventions of the present disclosure is an electromagnetic navigation system employing the aforementioned electromagnetic navigation device and a navigation controller for controlling a determination of the position and/or the orientation of the interventional tool relative to the guidewire responsive to a generation of the electromagnetic sensing data by the guidance/tracking electromagnetic sensors.

A third form of the inventions of the present disclosure is an electromagnetic navigation method for guiding and tracking the interventional tool within the anatomical region. The electromagnetic navigation method involves an insertion of a guidewire into the anatomical region with the guidewire including one or more guidance electromagnetic sensors generating guidance data informative of an electromagnetic sensing of a position and/or an orientation of the guidewire within the anatomical region.

The electromagnetic navigation method further involves a translation and/or a rotation of a hub in conjunction with the interventional tool relative to the guidewire with the hub including a tracking electromagnetic sensor generating tracking data informative of an electromagnetic sensing of a position and/or an orientation of the hub relative to the guidewire.

Collectively, the guidance data and the tracking data are informative of and electromagnetic sensing of a position and/or an orientation of the interventional tool relative to the guidewire.

The electromagnetic navigation method further involves a navigation controller, in response to the generation of the guidance data by the guidance electromagnetic sensor(s) and the generation of the tracking data by the tracking electromagnetic sensor, controlling a determination of the position and/or the orientation of the interventional tool relative to the guidewire.

For purposes of the inventions of the present disclosure, the terms "interventional tool", "guidewire", and "electromagnetic sensor" are to be interpreted as understood in the art of the present disclosure and as exemplary described herein.

Examples of interventional tools include, but are not limited to, a catheter, a stent-deployment system and a sheath.

Examples of devices deployable by an interventional tool include, but are not limited to, a balloon, a valve, a closure device, a clip, an endograft, an ablation catheter, a transseptal needle and a stent.

Examples of guidewires include, but are not limited to, a stiff guidewire, a floppy guidewire, a j-tipped guidewire and an FFR wire.

Examples of electromagnetic sensors include, but are not limited to, the electromagnetic sensors associated with commercially available electromagnetic tracking system (e.g., the Aurora electromagnetic tracking system by NDI).

For purposes of the present disclosure, the labels "guidance" and "tracking" as used herein for the term "electromagnetic sensor" distinguish each electromagnetic sensor for identification purposes as described and claimed herein without specifying or implying any additional limitation to the term "electromagnetic sensor".

For purposes of the inventions of the present disclosure, the term "data" is to be interpreted as understood in the art of the present disclosure and as exemplary described herein, and the labels "guidance" and "tracking" as used herein for the term "data" distinguish each data set for identification purposes as described and claimed herein without specifying or implying any additional limitation to the term "data".

For purposes of the present disclosure, the term "hub" broadly encompasses any structural entity having a configuration (1) adjoinable to the guidewire whereby the structural entity may be translated along and/or rotated about the guidewire or including a channel for extending the guidewire through the structural entity whereby the structural entity may be translated along and/or rotated about the guidewire, and (2) adjoinable to or integrated with the interventional tool whereby the structural entity in conjunction with the interventional tool may be translated along and/or rotated about the guidewire.

An example of a hub includes, but is not limited to, an annular hub aligned with a proximal end of an interventional tool whereby the hub may be translated along and/or rotated about the guidewire in conjunction with the interventional tool.

For purposes of the present invention, the term "adjoined" and any tense thereof broadly encompasses a detachable coupling, connection, affixation, clamping, mounting, etc. of components, and the term "integrated" and any tense thereof broadly encompasses a molding or a permanent coupling, connection, affixation, clamping, mounting, etc. of components.

For purposes of the present disclosure, the term "controller" broadly encompasses all structural configurations of an application specific main board or an application specific integrated circuit housed within or linked to a workstation for controlling an application of various inventive principles of the present disclosure as subsequently described herein. The structural configuration of the controller may include, but is not limited to, processor(s), computer-usable/computer readable storage medium(s), an operating system, application module(s), peripheral device controller(s), slot(s) and port(s).

For purposes of the present disclosure, the labels "electromagnetic sensor data", "imaging data", "navigation" and "X-ray" used herein for the term "controller" distinguish each controller for identification purposes as described and claimed herein without specifying or implying any additional limitation to the term "controller".

Examples of a "workstation" include, but are not limited to, an assembly of one or more computing devices, a display/monitor, and one or more input devices (e.g., a keyboard, joysticks and mouse) in the form of a client computer, a desktop or a tablet.

For purposes of the present disclosure, the term "application module" broadly encompasses a component of the workstation consisting of an electronic circuit and/or an executable program (e.g., executable software and/firmware) for executing a specific application.

The foregoing forms and other forms of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

DETAILED DESCRIPTION OF THE PREFERRED EMBODIMENTS

To facilitate an understanding of the various inventions of the present disclosure, the following description of FIGS. 1A-4C teaches basic inventive principles of an electromagnetic ("EM") navigation device employing an EM-sensed guidewire and an EM-sensed hub. From this description, those having ordinary skill in the art of the present disclosure will appreciate how to apply the inventive principles of the present disclosure for making and using numerous and various additional embodiments of electromagnetic navigation devices of the present disclosure. Please note the components of electromagnetic navigation devices and interventional tools of the present disclosure as shown in FIGS. 1A-4C are not drawn to scale, but drawn to conceptually visualize the inventive principles of the present disclosure.

Figure 1A:
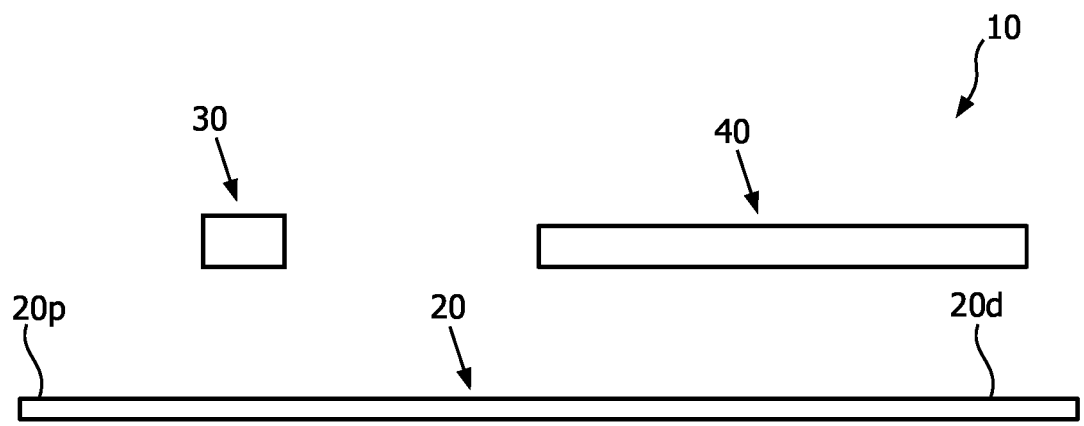
FIGS. 1A-1C illustrates exemplary embodiments of an electromagnetic navigation device in accordance with the inventive principles of the present disclosure.

Referring to FIG. 1A, an electromagnetic navigation device 10 of the present disclosure employs an EM-sensed guidewire 20, a EM-sensed hub 30 and an interventional tool 40 in an unassembled arrangement. Generally, when assembled, EM-sensed guidewire 20 serves to guide interventional tool 40 into an anatomical region as interventional tool 40 is translated along and/or rotated about EM-sensed guidewire 20. Prior to and/or during a guiding of interventional tool 40 into the anatomical region, EM-sensed hub 30 serves to track a positon and/or an orientation of interventional tool 40 relative to EM-sensed guidewire 20 as will be further described herein. To this end, EM-sensed hub 30 is adjoined to or integrated with interventional tool 40 to be translated along and/or rotated about EM-sensed guidewire 20 in conjunction with interventional tool 40.

By being adjoined to or integrated with interventional tool 40, EM-sensed hub 30 may be mapped 1-1 to any point of interventional tool 40 (e.g., a distal tip) or to any deployable device deployed by interventional tool 40 (e.g., a balloon, a valve, a endograft, a stent, etc.).

Furthermore, the tracking by the EM-sensed hub 30 of the position and/or orientation of interventional tool 40 relative to EM-sensed guidewire 20 may be utilized to display a virtual representation (e.g., an overlay) of interventional tool 40 and any deployable device within an image of the anatomical region (e.g., a magnetic resonance image, a computed-tomography image, an x-ray image, a positron emission tomography image, an ultrasound image and/or an optical image).

In practice, EM-sensed guidewire 20, a EM-sensed hub 30 and an interventional tool 40 may be assembled in any arrangement that facilitates the aforementioned guiding and tracking of interventional tool 40.

Figure 1B:
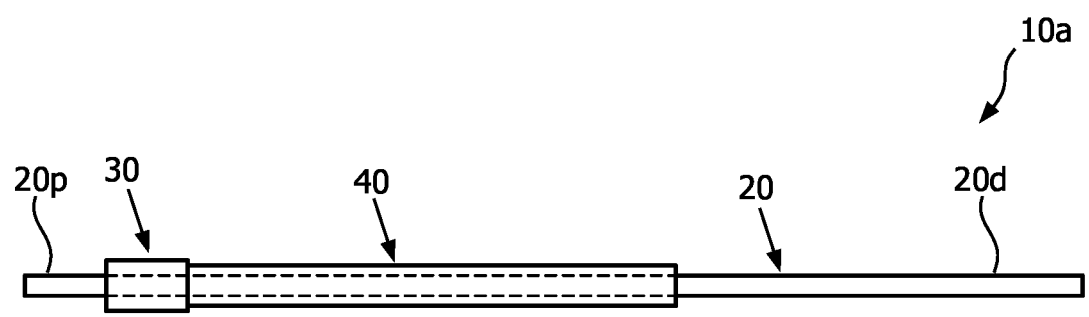

For example, FIG. 1B illustrates an embodiment 10a of electromagnetic navigation device 10 having an "over-the-wire" assembled arrangement of EM-sensed hub 30 and interventional tool 40 along EM-sensed guidewire 20 including EM-sensed hub 30 aligned with and adjoined to or integrated with a proximal end of interventional tool 40.

Figure 1C:
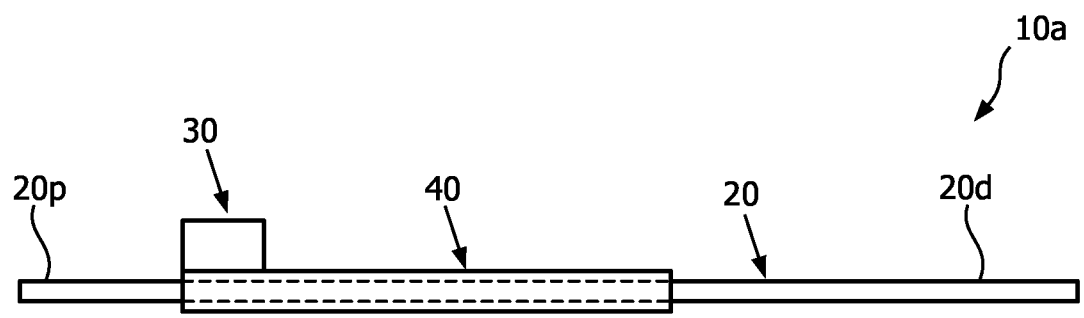

By further example, FIG. 1C illustrates an embodiment 10b of electromagnetic navigation device 10 having an "over-the-wire" assembled arrangement of interventional tool 40 along EM-sensed guidewire 20 including EM-sensed hub 30 adjoined to or integrated with an external surface of a proximal end of interventional tool 40.

From the examples of FIGS. 1B and 1C, those having ordinary skill in the art of the present disclosure will appreciate numerous and various additional assembled arrangements of EM-sensed guidewire 20, a EM-sensed hub 30 and an interventional tool 40.

Figure 5A:
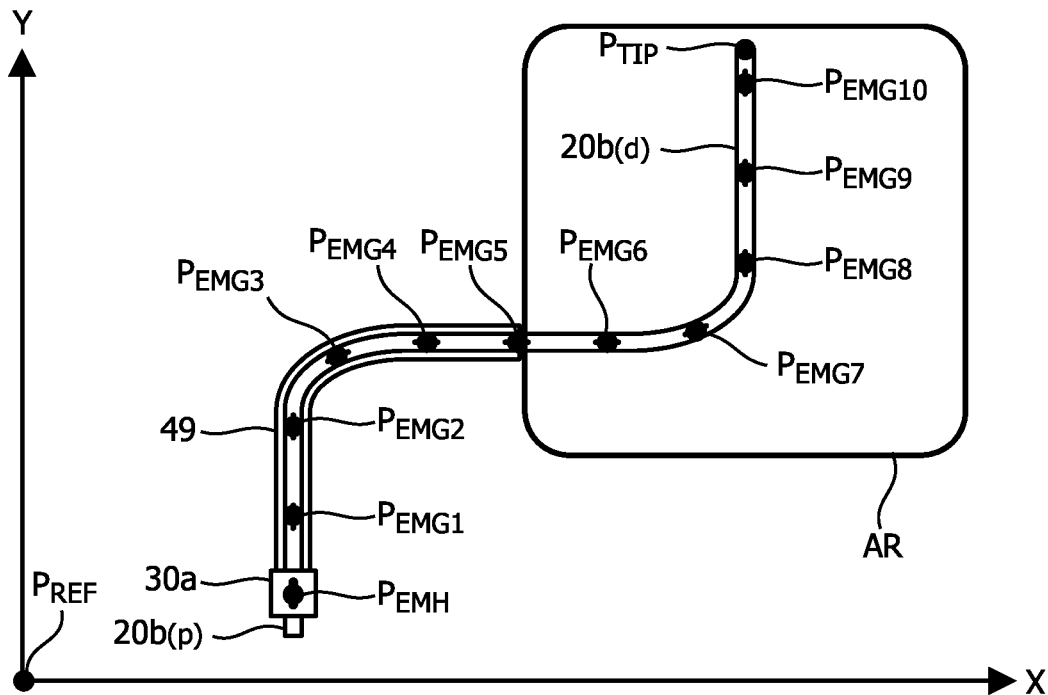
FIGS. 5A and 5B illustrate an exemplary passage of an EM-sensed hub and an interventional tool over an EM-sensed guidewire in accordance with the inventive principles of the present disclosure.
Figure 5B:
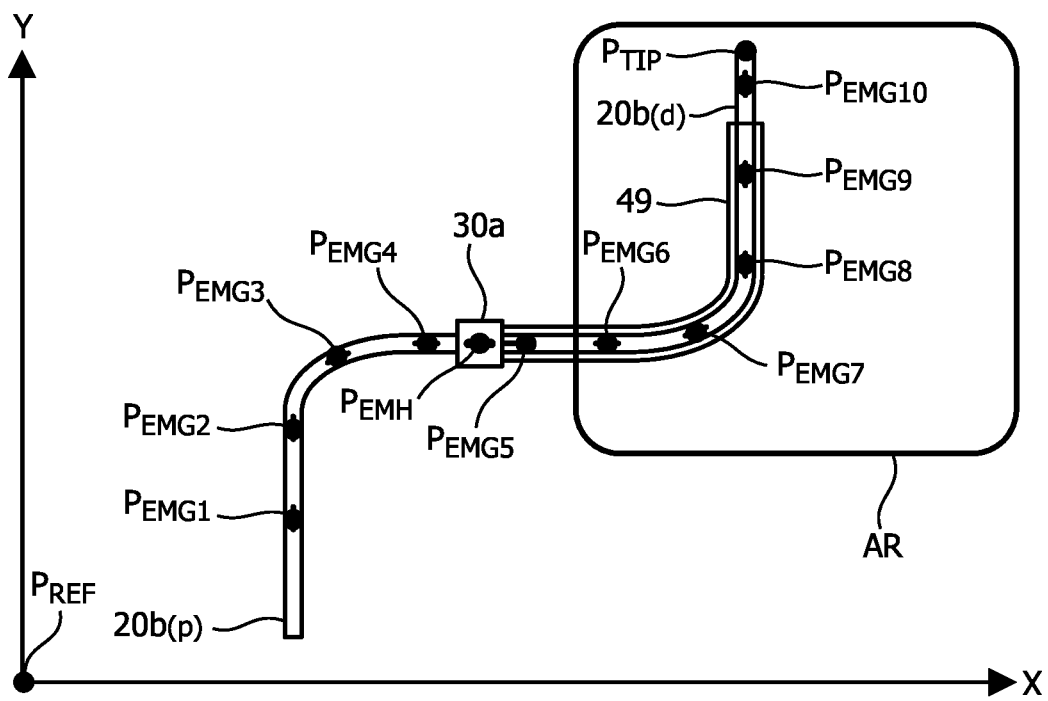

Referring back to FIG. 1A, in practice, EM-sensed guidewire 20 includes one (1) or more electromagnetic sensors (not shown in FIG. 1A) strategically adjoined to or integrated along a guidewire for generating guidance data informative of an electromagnetic sensing of a position and/or an orientation of EM-sensed guidewire 20 relative to an anatomical region as will be further described herein in connection with FIGS. 5A and 5B. Furthermore in practice, a stiffness of EM-sensed guidewire 20 and a degree of curvature of an intended anatomical path of EM-sensed guidewire 20 are factors for ascertaining an appropriate number and spacing of electromagnetic sensors adjoined to or integrated with EM-sensed guidewire 20.

Figure 2A:
FIGS. 2A and 2B illustrates exemplary embodiments of an EM-sensed guidewire in accordance with the inventive principles of the present disclosure.

For example, FIG. 2A illustrates an embodiment 20a of EM-sensed guidewire 20 having an electromagnetic sensor 21p adjoined to or integrated with a guidewire 22 adjacent a tip of a proximal segment of guidewire 22, and an electromagnetic sensor 21d adjoined to or integrated with guidewire 22 adjacent a tip of distal segment of guidewire 22. In operation, electromagnetic sensors 21p and 21d generate guidance data informative of an electromagnetic sensing of a position and/or an orientation of EM-sensed guidewire 20a relative to an anatomical region. While EM-sensed guidewire 20a is not limited to any particular application, EM-sensed guidewire 20a is suitable for applications requiring a significant degree of stiffness of guidewire 22 and/or a minimal degree of curvature of guidewire 22 within the anatomical region (e.g., a deployment of an endograft over a stiff guidewire).

Figure 2B:
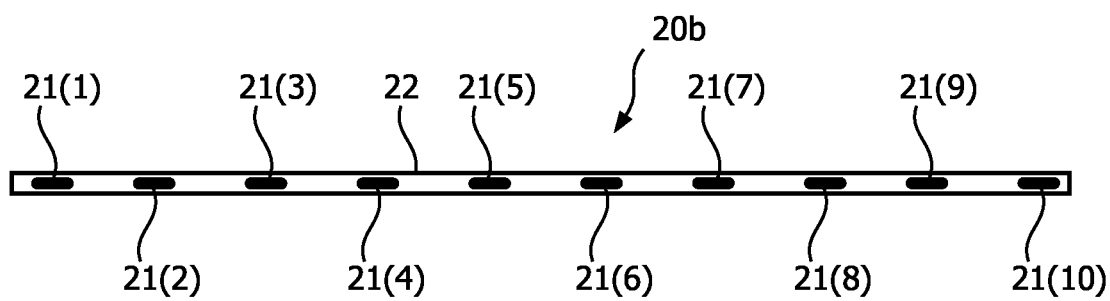

By further example, FIG. 2B illustrates an embodiment 20b of EM-sensed guidewire 20 having ten (10) equally spaced electromagnetic sensors 21 adjoined to or integrated with guidewire 22. In operation, electromagnetic sensors 21 generate guidance data informative of an electromagnetic sensing of a position and/or an orientation of EM-sensed guidewire 20b relative to an anatomical region. While EM-sensed guidewire 20b is not limited to any particular application, EM-sensed guidewire 20b is suitable for applications requiring a more flexibility than guidewire and/or a significant degree of curvature of guidewire 22 within the anatomical region (e.g., navigation of a flexible catheter or sheath over a floppy guidewire).

Furthermore, referring back to FIG. 1A, proximal segment 20p of EM-sensed guidewire 20 may or may not be stiffer than the distal segment 20d of EM-sensed guidewire 20, and/or proximal segment 20p of EM-sensed guidewire 20 may or may not be experience a higher degree of curvature than the distal segment 20d of EM-sensed guidewire 20 within the anatomical region. For any such differences, the electromagnetic sensors may be unevenly distributed and/or spaced within proximal segment 20p and distal segment 20d. Different applications may also require different accuracy thereby leading to different EM sensor integration profiles.

For example, referring to FIG. 2B, a modified version of EM-sensed guidewire 20b may include two (2) electromagnetic sensors 21 within the proximal segment of guidewire 22 and further include eight (8) electromagnetic sensors 21 within the distal segment of guidewire 22 for applications requiring a stiffer distal segment and/or a higher degree of curvature of the distal segment.

From the examples of FIGS. 2A and 2B, those having ordinary skill in the art of the present disclosure will appreciate numerous and various additional embodiments of EM-sensed guidewire 20.

Referring back to FIG. 1A, in practice, EM-sensed hub 30 includes one (1) or more electromagnetic sensors (not shown in FIG. 1A) strategically adjoined to or integrated with EM-sensed hub 30 for generating tracking data informative of an electromagnetic sensing of a position and/or an orientation of EM-sensed hub 30 relative to guidewire 20 as will be further described herein. Also in practice, EM-sensed hub 30 may have any structural configuration suitable to adjoin or integrate EM-sensed hub 30 with interventional tool 40 for purposes of tracking interventional tool 40.

Figure 3A:
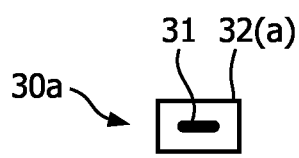
FIGS. 3A-3E illustrates exemplary embodiments of an EM-sensed hub in accordance with the inventive principles of the present disclosure.
Figure 3B:
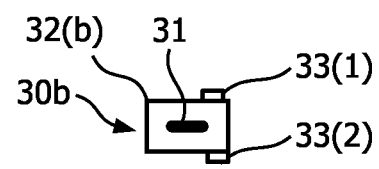
Figure 3C:
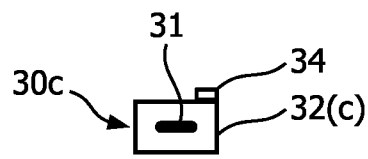
Figure 3D:
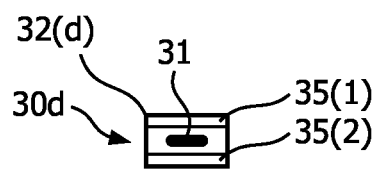
Figure 3E:
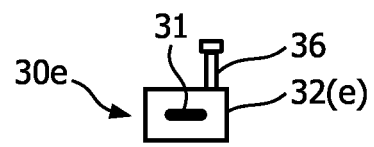

For example, FIGS. 3A-3E illustrates respective embodiments 30a-30e of EM-sensed hub 30 having a single electromagnetic sensor 31 adjoined to or integrated with an annular hub 32. More particularly, FIG. 3A illustrates EM-sensed hub 30a having electromagnetic sensor 31 adjoined to or integrated with annular hub 32a. FIG. 3B illustrates EM-sensed hub 30b having electromagnetic sensor 31 adjoined to or integrated with annular hub 32b including a pair of radio-opaque markers 33 for registration of EM-sensed hub 30b. FIG. 3C illustrates EM-sensed hub 30c having electromagnetic sensor 31 adjoined to or integrated with annular hub 32c including a dot or bump 34 for visual or tactile orientation of EM-sensed hub 30b. FIG. 3D illustrates EM-sensed hub 30d having electromagnetic sensor 31 adjoined to or integrated with annular hub 32d including grooves 35 for selective torqueing of EM-sensed hub 30d, and, FIG. 3E illustrates EM-sensed hub 30e having electromagnetic sensor 31 adjoined to or integrated with annular hub 32e including a locking mechanism in the form of a screw 36 for fixing the relative positons of EM-sensed guidewire 20 (FIG. 1) and EM-sensed hub 30e.

From the examples of FIGS. 3A-3E, those having ordinary skill in the art of the present disclosure will appreciate numerous and various additional embodiments of EM-sensed hub 30.

Referring back to FIG. 1A, in practice, interventional tool 40 may be any type of interventional tool suitable as an "over-the-wire" tool or adjoinable adjacent to guidewire 20 including, but not limited to, a catheter, a stent-deployment system and sheath. Furthermore, for embodiments of interventional tool 40 having a deployment device (e.g., a balloon, valve, stent, etc.), an additional tracking electromagnetic sensor may be adjoined to or integrated with the deployment device for tracking a position and/or orientation of the deployment device relative to guidewire 20 as will be further described herein.

Figure 4A:
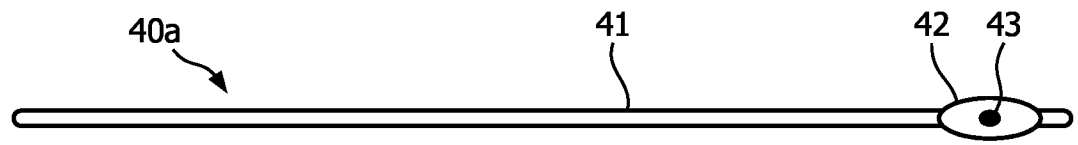
FIGS. 4A-4C illustrates exemplary embodiments of an EM-sensed interventional tool in accordance with the inventive principles of the present disclosure.

For example, FIG. 4A illustrates an embodiment 40a of interventional tool 40 having a catheter 41, a deflated balloon 42 and an additional tracking electromagnetic sensor 43 adjoined to or integrated with deflated balloon 42 for tracking an inflation of balloon 42.

Figure 4B:
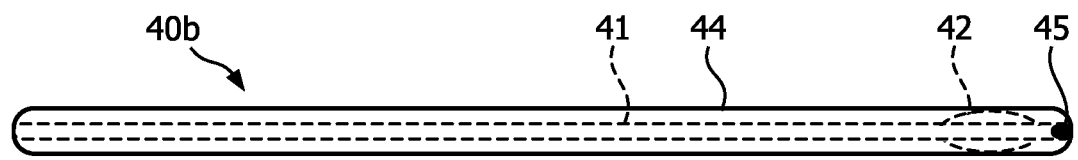

By further example, FIG. 4B illustrates an embodiment 40b of interventional tool 40 having a sheath 44 covering catheter 41 and deflated balloon 42, and an additional tracking electromagnetic sensor 43 adjoined to or integrated with sheath 44 for tracking a withdrawal of sheath 44 over catheter 41.

Figure 4C:
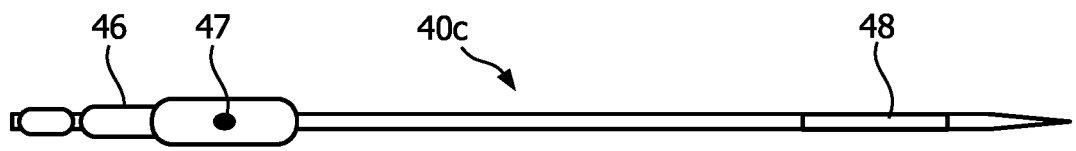

Also by example, FIG. 4C illustrates an embodiment 40c of interventional tool 40 in the form of a stent-deployment system having a handle 46 and an additional tracking electromagnetic sensor 47 adjoined to or integrated with handle 46 for tracking a deployment of a stent 48.

From the examples of FIGS. 4A-4C, those having ordinary skill in the art of the present disclosure will appreciate numerous and various additional embodiments of EM-sensed hub 30.

Referring back to FIG. 1A, EM-sensed hub 30 and interventional tool 40 are adjoined or integrated to be collectively translated along and/or rotated about guidewire 20 in an "over-the-wire" manner and/or adjacent guidewire 20. In practice, any technique may be implemented for adjoining or integrating EM-sensed hub 30 and interventional tool 40 including, but not limited to, a luer-lock attachment onto a proximal end of interventional tool 40, a mechanical attachment (e.g., a clip or a clamp), an adhesive and a single-piece manufacturing.

Additionally, in practice, EM-sensed hub 30 interventional tool 40 as adjoined or integrated may be back-loaded or front-loaded on EM-sensed guidewire 20 in an "over-the-wire" manner and/or adjacent guidewire 20.

To facilitate a further understanding of the various inventions of the present disclosure, the following description of FIGS. 5A-7C teaches basic inventive principles of guiding and tracking an interventional tool by an EM-sensed guidewire and an EM-sensed hub. From this description, those having ordinary skill in the art of the present disclosure will appreciate how to apply the inventive principles of the present disclosure for making and using numerous and various additional embodiments of guiding and tracking an interventional tool by an EM-sensed guidewire and an EM-sensed hub of the present disclosure.

Please note FIGS. 5A-7C are described in the context of EM-sensed guidewire 20b (FIG. 2B), EM-sensed hub 30a (FIG. 3A) and a catheter 49. Nonetheless description of FIGS. 5A-7C is applicable to numerous and various embodiments of the present disclosure. Also note that FIGS. 5A and 5B illustrate a planar view of a three-dimensional ("3D") of an anatomical region AR (e.g., a cephalic region, a cervical region, a thoracic region, an abdominal region, a pelvic region, etc.). As shown, EM-sensed hub 30a typically in practice will not be inserted within the anatomical region AR for purposes.

Referring to FIGS. 5A and 5B, for guiding purposes of catheter 49, EM-sensed guidewire 20b is inserted within anatomical region AR. The guidance electromagnetic sensors 21 of EM-sensed guidewire 20b are operated to generate guidance data informative of an electromagnetic sensing of a position and/or an orientation of EM-sensed guidewire 20b within anatomical region AR. More particularly, in the presence of an electromagnetic field generator (not shown), guidance electromagnetic sensors 21 generate ten (10) reference position signals $P_{EMG}$ relative to a reference position $P_{REF}$. Reference position signals $P_{EMG}$ collectively represent guidance data informative of the position and/or the orientation of EM-sensed guidewire 20b within anatomical region AR.

For tracking purposes of catheter 49, EM-sensed hub 30 and catheter 49 as adjoined or integrated are passed over EM-sensed guidewire 20b into anatomical region AR. The tracking electromagnetic sensor 31 of EM-sensed hub 30a is operated to generate tracking data informative of an electromagnetic sensing of a position and/or an orientation of EM-sensed hub 30a within anatomical region AR. More particularly, in the presence of an electromagnetic field generator (not shown), tracking electromagnetic sensor 31 generates a reference position signal $P_{EMH}$ relative to reference position $P_{REF}$. Reference position signal $P_{EMH}$ represents tracking data informative of the position and/or the orientation of EM-sensed hub 30a relative to guidewire 20b.

From the guiding and tracking of catheter 49, a position and/or an orientation of catheter 49 within anatomical region AR may be determined as EM-sensed hub 30 and catheter 49 as adjoined or integrated are passed over EM-sensed guidewire 20b into anatomical region AR. In practice, the determination of the position and/or the orientation of catheter 49 within anatomical region AR may be focused on a particular point of catheter 49 (e.g., a distal tip of catheter 49) or a particular segment of catheter 49 (e.g., a distal segment of catheter 49).

More particularly, the determination of the position and/or the orientation of catheter 49 within anatomical region AR is derived from an interpolation of a distance of sensed reference position $P_{EMH}$ of tracking electromagnetic sensor 31 of EM-sensed hub 30 from sensed reference positions $P_{EMG}$ of two (2) or more guidance electromagnetic sensors 22 of EM-sensed guidewire 20b. The sensor distance interpolation facilitates a guidewire position projection of tracking electromagnetic sensor 31 upon an alignment of the guidance electromagnetic sensors 22 of EM-sensed guidewire 20c, and the guidewire position projection facilitates a determination of the position and/or the orientation of catheter 49 within anatomical region AR based on a combined length of EM-sensed hub 30a and catheter 49 relative to a larger length of EM-sensed guidewire 20b.

Figure 6:
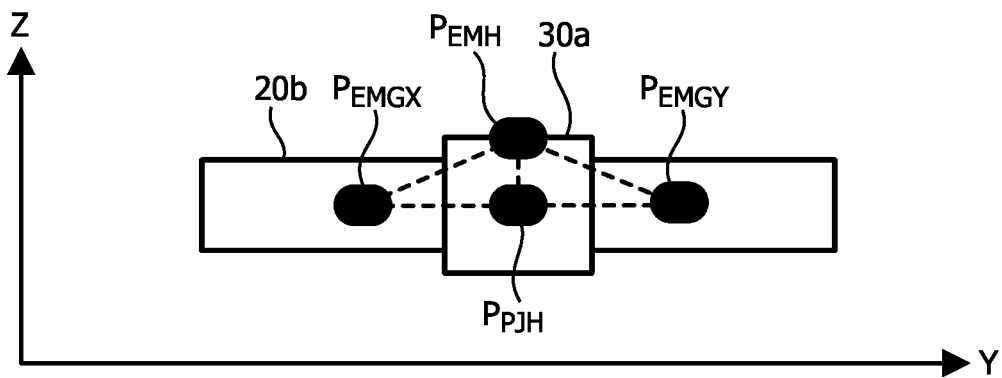
FIG. 6 illustrates an exemplary projection of a position of a tracking electromagnetic sensor of an EM-sensed hub onto an EM-sensed guidewire in accordance with the inventive principles of the present disclosure.

For example, FIG. 6 illustrates an interpolation of a distance between a sensed reference position $P_{EMGX}$ of a guidance electromagnetic sensor 21X and a sensed reference position $P_{EMH}$ of tracking electromagnetic sensor 31, and an interpolation of a distance between a sensed reference position $P_{EMGY}$ of guidance electromagnetic sensor 21Y and a reference position $P_{EMH}$ position of tracking electromagnetic sensor 31 whereby a guidewire position $P_{PJH}$ of tracking electromagnetic sensor 31 may be projected unto an alignment of guidance electromagnetic sensors 21X and 21Y.

Alternatively, an interpolation of the distance between the sensed reference position $P_{EMGX}$ of the guidance electromagnetic sensor 21X and a sensed reference position $P_{EMH}$ of tracking electromagnetic sensor 31 may be utilized to project guidewire position $P_{PJH}$ of tracking electromagnetic sensor 31 unto guidewire 20b.

In practice, as described for FIG. 6, one (1) or more guidance electromagnetic sensors 21 may be utilized for the sensor distance interpolation/guidewire position projection. For embodiments having two (2) or more guidance electromagnetic sensors 21, the closest guidance electromagnetic sensor 21 proximal to tracking electromagnetic sensor 31 and the closest guidance electromagnetic sensor 21 distal to tracking electromagnetic sensor 31 may be utilized for the sensor distance interpolation/guidewire position projection.

For a determination of the position and/or the orientation of catheter 49 within anatomical region AR, a length $L_{GW}$ of EM-sensed guidewire 20b, a length $L_{HUB}$ of EM-sensed hub 30a and a length $L_{CAT}$ of catheter 49 are known either by construction and/or calibration. Additionally, respective position lengths $L_{EMG1}$-$L_{EMG10}$ of guidance electromagnetic sensors 21(1)-21(10) as adjoined to or integrated within EM-sensed guidewire 20b is known either by construction and/or calibration.

From the sensor distance interpolation/guidewire position projection, the position and/or the orientation of catheter 49 within anatomical region AR is determined based on the known combined length $L_{HUB}$+$L_{CAT}$ of EM-sensed hub 30a and catheter 49 relative to the known larger length $L_{GW}$ of EM-sensed guidewire 20b.

Figure 7A:
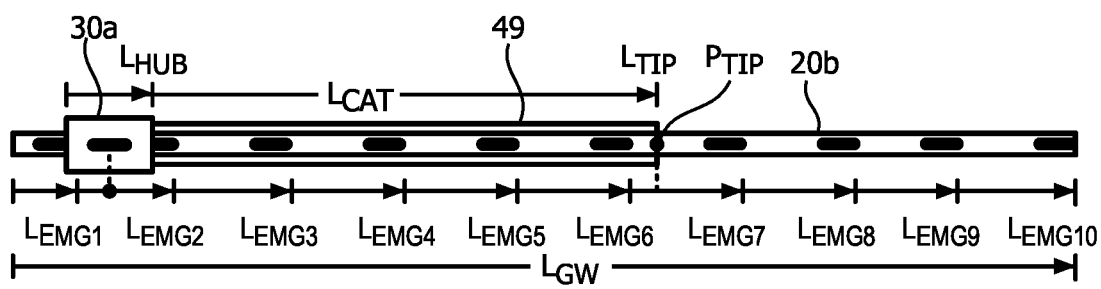
FIGS. 7A-7C illustrate exemplary determinations of a position of a tip of an interventional tool relative to an EM-sensed guidewire in accordance with the inventive principles of the present disclosure.

For example, FIG. 7A illustrates a one-dimensional ("1D") alignment of lengths $L_{GW}$, $L_{HUB}$ and $L_{CAT}$ derived from a sensor distance interpolation/guidewire positon projection that projected tracking electromagnetic sensor 31 of EM-sensed hub 30 between guidance electromagnetic sensors 21(1) and 21(2) as shown. Consequently, length $L_{TIP}$ of a distal tip of catheter 49 is between guidance electromagnetic sensors 21(6) and 21(7) as shown whereby a reference position $P_{TIP}$ of the distal tip of catheter 49 within anatomical region AR is derived from an interpolation of respective distances of distal tip length $L_{TIP}$ from the respective sensed reference positions $P_{EMG6}$ and $P_{EMG7}$ (FIGS. 5A & 5B) of guidance electromagnetic sensors 21(6) and 21(7).

Figure 7B:
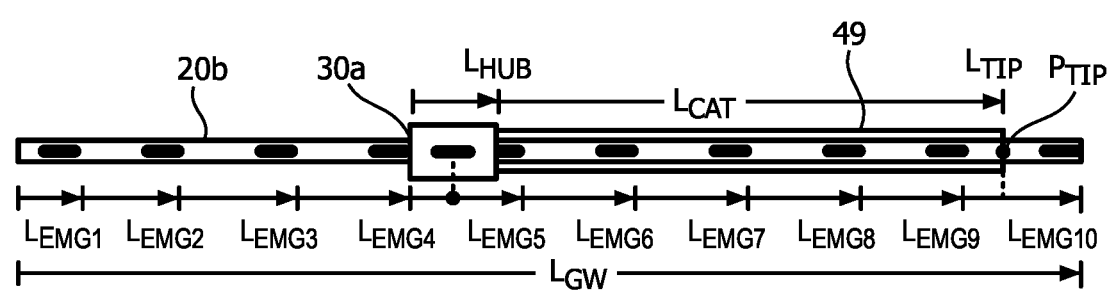

By further example, FIG. 7B illustrates a 1D alignment of lengths $L_{GW}$, $L_{HUB}$ and $L_{CAT}$ derived from a sensor distance interpolation/guidewire positon projection that projected tracking electromagnetic sensor 31 of EM-sensed hub 30 between guidance electromagnetic sensors 21(4) and 21(5) as shown. Consequently, length $L_{TIP}$ of a distal tip of catheter 49 is between guidance electromagnetic sensors 21(9) and 21(10) as shown whereby a reference position $P_{TIP}$ of the distal tip of catheter 49 within anatomical region AR is derived from an interpolation of respective distances of distal tip length $L_{TIP}$ from the sensed reference positions $P_{EMG9}$ and $P_{EMG10}$ (FIGS. 5A & 5B) guidance electromagnetic sensors 21(9) and 21(10).

Figure 7C:
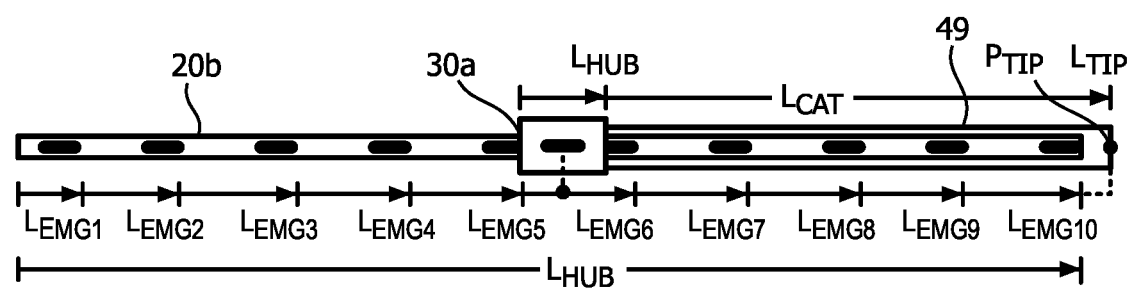

Also by example, FIG. 7C illustrates a 1D alignment of lengths $L_{GW}$, $L_{HUB}$ and $L_{CAT}$ derived from a sensor distance interpolation/guidewire positon projection that projected tracking electromagnetic sensor 31 of EM-sensed hub 30 between guidance electromagnetic sensors 21(5) and 21(6) as shown. Consequently, length $L_{TIP}$ of a distal tip of catheter 49 extends beyond guidance electromagnetic sensor 21(10) as shown whereby a position and/or an orientation of the distal tip of catheter 49 within anatomical region AR may be derived from any technique suitable for predicting a reference position $P_{TIP}$ of the distal tip of catheter 49 within anatomical region AR relative to the sensed reference positions $P_{EMG10}$ (FIGS. 5A & 5B) of guidance electromagnetic sensor 21(10).

One technique involves an extrapolation along a vector of $P_{EMG10}$ for a length of $L_{CAT}$ that extends beyond length $L_{EMG10}$. A second technique involves a prediction of reference position $P_{TIP}$ using other information such as the properties of catheter 49, a known configuration of anatomical region AR, and an imaging of anatomical region AR. A third technique involves utilization of a probability map of likely reference positions $P_{TIP}$.

From the examples of FIGS. 5A-7C, those having ordinary skill in the present disclosure will appreciate numerous and various implementations of a sensor distance interpolation/guidewire positon projection.

Figure 8A:
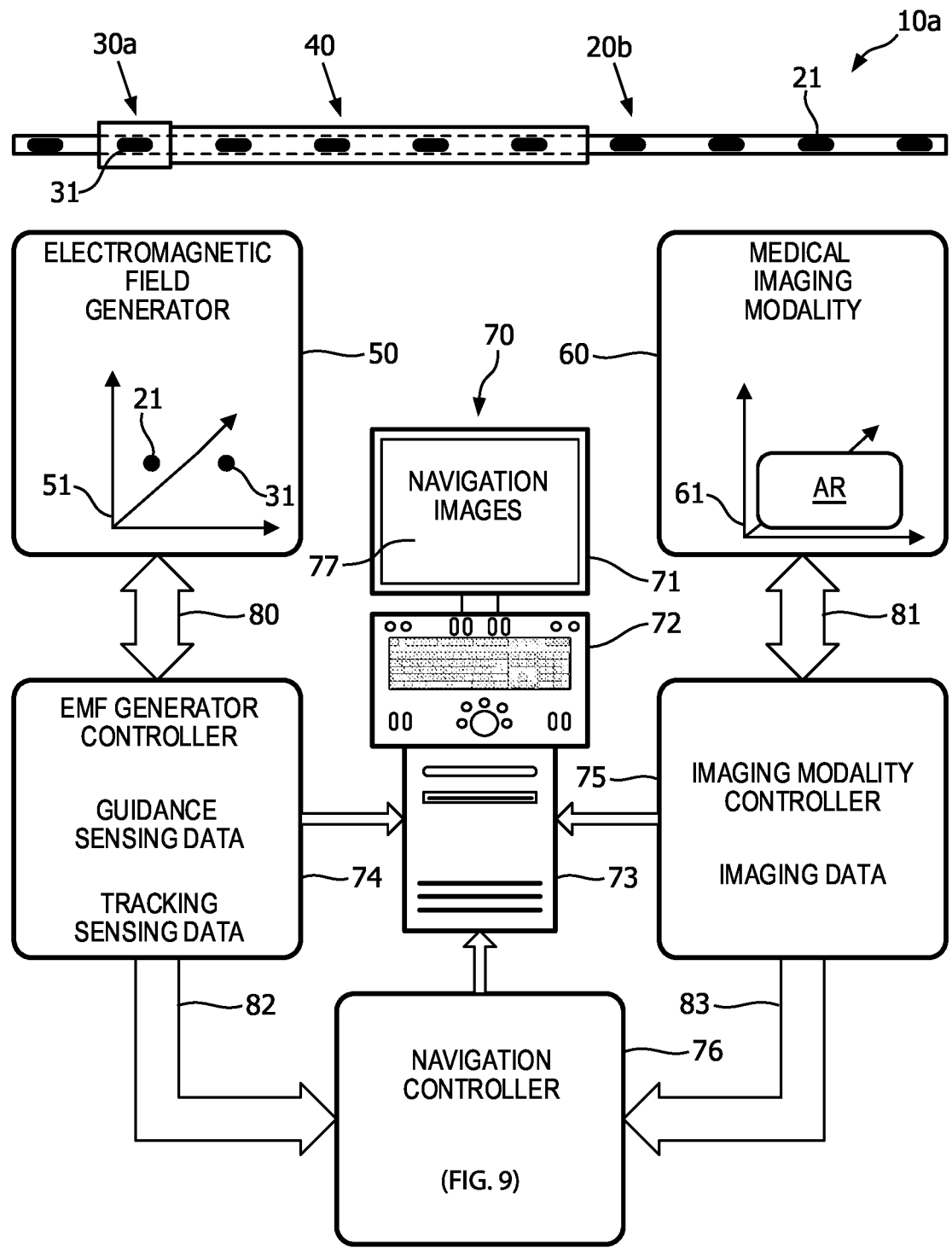
FIG. 8A illustrates an exemplary embodiment of an electromagnetic navigation system for various applications in accordance with the inventive principles of the present disclosure.
Figure 8B:
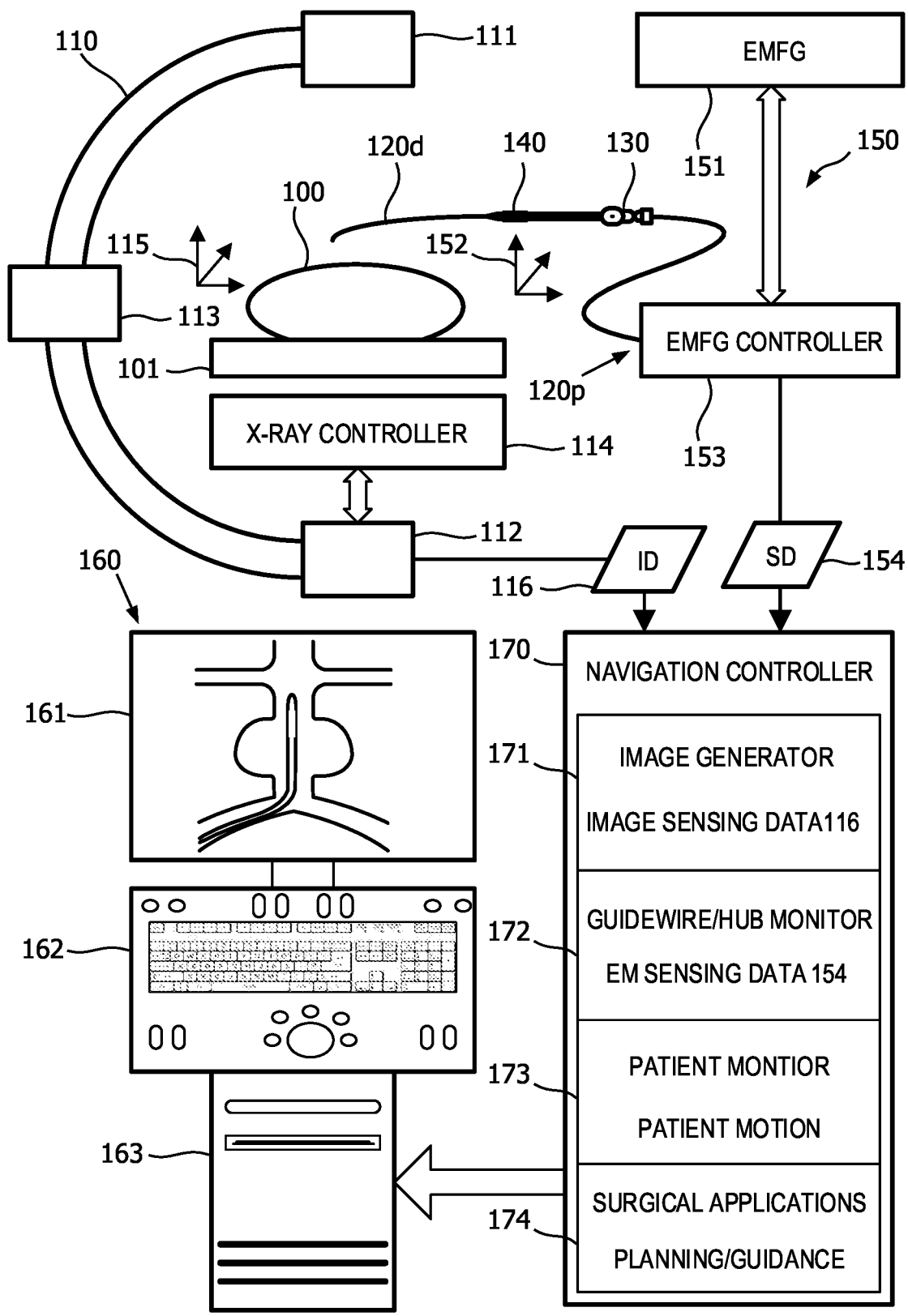
FIG. 8B illustrates an exemplary embodiment of an electromagnetic navigation system for an endovascular aneurysm repair procedure in accordance with the inventive principles of the present disclosure.
Figure 9:
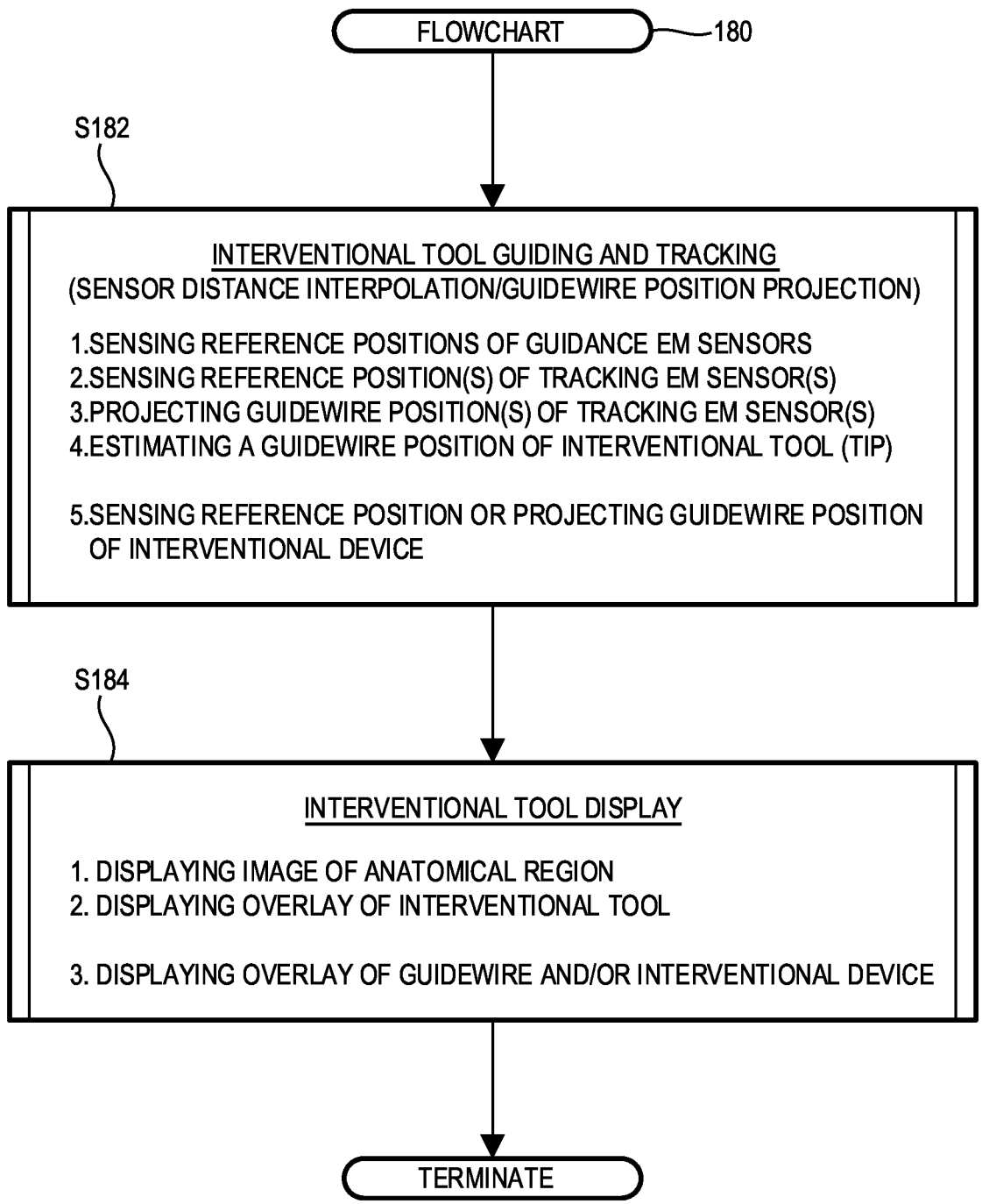
FIG. 9 illustrates a flowchart of an exemplary embodiment of an electromagnetic navigation method in accordance with the inventive principles of the present disclosure.

To facilitate a further understanding of the various inventions of the present disclosure, the following description of FIGS. 8A and 8B teaches basic inventive principles of electromagnetic navigation systems of the present disclosure. From this description, those having ordinary skill in the art of the present disclosure will appreciate how to apply the inventive principles of the present disclosure for making and using numerous and various additional embodiments electromagnetic navigation systems of the present disclosures. Please note the components of an electromagnetic navigation devices and interventional tools of the present disclosure as shown in FIGS. 8A-9 are not drawn to scale, but drawn to conceptually visualize the inventive principles of the present disclosure.

Referring to FIG. 8A, an electromagnetic navigation system of the present disclosure, generally applicable to numerous and various procedures, employs EM-sensed guidewire 20b (FIG. 2B), EM-sensed hub 30a (FIG. 3A), interventional tool 40 (FIG. 1), an electromagnetic field generator 50, a medical imaging modality 60 and a workstation 70 including a known arrangement of a monitor 71, a keyboard 72 and a computer 73. An electromagnetic sensor data controller 74, an imaging data controller 75 and a navigation controller 76 are installed within workstation 70 for executing an electromagnetic navigation method of the present disclosure as will be further described herein.

As known in the art, electromagnetic field generator 50 is operated by EM sensor data controller 74 via a communication channel 80 for generating electromagnetic field (not shown) within a reference coordinate system 51 occupied by electromagnetic sensors 21 and 31 of EM-sensed guidewire 20 and EM-sensed hub 30, respectively, whereby EM sensor data controller 74 receives guidance sensing data from guidance electromagnetic sensors 21 and tracking sensing data from tracking electromagnetic sensor 31 as previously described herein in connection with FIGS. 5A-7C.

Alternatively to be installed on workstation 70, electromagnetic sensor data controller 74 may be installed on an electromagnetic field generator workstation as known in the art.

As known in the art, medical imaging modality 60 (e.g., a magnetic resonance modality, a computed-tomography modality, an x-ray modality, a positron emission tomography modality, an ultrasound modality and/or an optical modality) is operated by imaging data controller 75 via a communication channel 81 for generating imaging data illustrative of anatomical region AR within an imaging coordinate system 61.

Alternatively to be installed on workstation 70, imaging data controller 75 may be installed on an medical imaging modality workstation as known in the art.

Navigation controller 76 receives the EM sensing data from EM sensor data controller 74 via a communication channel 82 and receives the imaging data from imaging data controller 75 via a communication channel 83 for processing the EM sensing data and the imaging data to determine a position and/or an orientation of interventional tool 40 within an anatomical region AR that is derived from a sensor distance interpolation/guidewire positon projection of the electromagnetic sensors of EM-based guidewire 20 and EM-sensed hub 30 as previously exemplary described herein as will be further described herein in connection with FIG. 9.

From the position/orientation determination of interventional tool 40, navigation controller 76 renders a display of navigation images 77 on monitor 71 whereby navigation images 77 are illustrative of a guided and tracked interventional tool 40 and tracked guidewire 21 represented within the images of anatomical region AR as will be further described herein in connection with FIG. 9.

Referring to FIG. 8B, an electromagnetic navigation system of the present disclosure, applicable for a EVAR procedure, employs a fluoroscopic imager 110, an EM-sensed guidewire 120, an EM-sensed hub 130, a stent-deployment device 140, an electromagnetic field generation system 150, and a workstation 160 including a known arrangement of a monitor 161, a keyboard 162 and a computer 163.

As known in the art, fluoroscopic imager 110 generally includes an X-ray generator 111, an image intensifier 112 and a collar 113 for rotating fluoroscopic imager 110. In operation, fluoroscopic imager 110 generates imaging data 116 as controlled by an X-ray controller 114 whereby imaging data 116 is illustrative of a fluoroscopic image of an anatomical area of patient 100 lying prone on an operating table 101 within an imaging coordinate system 115. X-ray controller 114 may be installed on workstation 150 or alternatively installed on an imaging workstation as known in the art.

As known in the art, electromagnetic field generation system 150 generally includes an electromagnetic field generator ("EMFG") 151, EFMG controller 153 and electromagnetic sensors (not shown) adjoined to or integrated within EM-sensed guidewire 120 and EM-sensed hub 130. In operation, EMFG controller 153 controls a generation by EFMG 151 generates of electromagnetic field (not shown) within an EMF coordinate system 152 occupied by the electromagnetic sensors whereby the electromagnetic sensors generate EM sensing data 144 informative of a position and/or an orientation of EM-sensed guidewire 120 and EM-sensed hub 130 within EMF coordinate system 152.

A navigation controller 170 is installed within workstation 160 for executing an electromagnetic navigation method of the present disclosure as will be further described herein in connection with FIG. 9. Navigation controller 70 includes application modules in the form of an image generator 171, a guidewire/hub monitor 172, a patient monitor 173 and surgical application(s) 174.

Image generator 171 processes imaging sensing data 116 for generating fluoroscopic images for display as known in the art.

Guidewire/hub monitor 172 processes EM sensing data 144 for monitoring a position and/or an orientation of EM-sensed guidewire 120 within anatomical region 100 and for monitoring a position and/or an orientation of EM-sensed hub 130 relative to EM-sensed guidewire 120.

Patient monitor 173 monitors a motion of patient 100 within imaging coordinate system 115 as known in the art.

Surgical applications 174 includes one or more known applications for performing the surgical procedure including, but not limited to, an image planning application for plaining trajectories and positioning of stent-deployment device 140 for deployment of a stent (not shown) within patient 100, and an image guidance application for displaying an overlay of stent-deployment device 140 and the stent onto the generated fluoroscopic images as exemplary shown in FIG. 8B and/or operative images registered to the generated fluoroscopic images. Examples of the operative images include, but are not limited to, a pre-operative and/or an intra-operative CT and MRI images.

More particularly, based on a registration of coordinate systems 115 and 152, the image guidance application determines a position and/or an orientation of stent-deployment device 140 within patient 100 that is derived from a sensor distance interpolation/guidewire positon projection of the electromagnetic sensors of EM-based guidewire 120 and EM-sensed hub 130 as previously exemplary described herein as will be further described herein in connection with FIG. 9. This determination enables the image guidance application to generate a virtual representation of stent-deployment device 150 within the generates fluoroscopic image and/or registered operative image.

To facilitate a further understanding of the various inventions of the present disclosure, the following description of FIG. 9 teaches basic inventive principles of electromagnetic navigation methods of the present disclosure. From this description, those having ordinary skill in the art of the present disclosure will appreciate how to apply the inventive principles of the present disclosure for making and using numerous and various additional embodiments electromagnetic navigation methods of the present disclosures. Please note, in practice of an electromagnetic navigation method of the present disclosure, a complexity of a sensor distance interpolation/guidewire positon projection of the electromagnetic sensors of an EM-sensed guidewire and EM-sensed hub is dependent upon the number of electromagnetic sensors and a degree of stiffness and planned curvature of the EM-sensed guidewire. Consequently, to minimize the number of electromagnetic sensors of an EM-sensed guidewire and EM-sensed hub, the present disclosure proposes various techniques including, but not limited to, a utilization of anatomical constraints derived from intraoperative or pre-operative imaging of the anatomical region, a utilization of guidewire mechanical characteristics to understand the curvature limitations of the interventional tool, and a utilization of an intraoperative image (e.g., a fluoroscopic image) to capture the guidewire curvature/position as the hub and interventional tool are passed over the guidewire.

Referring to FIG. 9, a flowchart 180 represents an electromagnetic navigation method of the present disclosure.

A stage S182 of flowchart 180 encompasses a guiding and a tracking of an interventional tool by a navigation controller of the present disclosure derived from a sensor distance interpolation/guidewire position projection technique of the present disclosure. Generally, an execution of a sensor distance interpolation/guidewire position projection technique of the present disclosure during stage S182 as EM-sensed hub and an interventional tool are passed over an EM-sensed guidewire includes:
(1) a sensing of reference positions of guidance EM sensors of an EM-sensed guidewire as exemplary illustrated in FIGS. 5A and 5B;
(2) a sensing of reference position(s) of tracking EM sensor(s) of an EM-sensed hub as exemplary illustrated in FIGS. 5A and 5B;
(3) a projection of a guidewire position(s) of tracking EM sensor(s) of the EM-sensed hub as exemplary illustrated in FIG. 6; and
(4) an estimating a guidewire position of an interventional tool as exemplary illustrated in FIGS. 7A-7C.

The execution of a sensor distance interpolation/guidewire position projection technique of the present disclosure during stage S182 as EM-sensed hub and an interventional tool are passed over an EM-sensed guidewire may further include a EM sensing of a reference position or a projection of a guidewire positon of an interventional device deployed by the interventional tool (e.g., a balloon of a catheter and a stent of a stent-deployment device).

A stage S184 of flowchart 180 encompasses a display of a virtual representation of the interventional tool derived from the guiding and tracking of the interventional tool during stage S182. Generally, as EM-sensed hub and an interventional tool are passed over an EM-sensed guidewire, stage S184 includes a display of an image of the anatomical region with a display of an overlay of the interventional tool as known in the art.

Additional features of stage S184 may include, but are not limited to:
(1) a registration of a key feature of an unsensed interventional device such as the position of an endograft using intraoperative imaging, pre-op imaging of the device, or known mechanical positioning;
(2) a tracking of orientation by tracking the hub orientation in space and using a mapping between the hub and the distal part of the device (in endograft deployment, this can be close to a 1-to-1 relationship);
(3) a visualization and a positioning of a model along the unsensed device (e.g., endograft, balloon catheter, or other therapy device); and
(4) a tracking the state of deployment of therapy by putting an additional EM sensor on a portion of interventional tools. For example, in endograft systems, this could be on the sliding handle that deploys the endograft. With the EM-sensed hub tracking the proximal part of the deployment system, then the attachment of one additional EM sensor onto the sliding handle would be informative of a state of deployment of the endograft, which could then be modelled and shown to the operator (thus eliminating the need for x-ray).

Stages S182 and S184 are continually executed until the terminate of flowchart 180.

Referring to FIGS. 1-9, those having ordinary skill in the art of the present disclosure will appreciate numerous benefits of the present disclosure including, but not limited to, an electromagnetic guidance and a tracking by a guidewire and a hub of an interventional tool (e.g., a catheter, a stent-deployment device, a sheath, etc.) within an anatomical area for various applications. Examples of such applications include, but are not limited to, vascular procedures, endoluminal procedures, orthopedic procedures and non-medical applications.

Further, as one having ordinary skill in the art of the present disclosure will appreciate in view of the teachings provided herein, features, elements, components, etc. described in the present disclosure/specification and/or depicted in the Figures may be implemented in various combinations of hardware and software, and provide functions which may be combined in a single element or multiple elements. For example, the functions of the various features, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of novel and inventive electromagnetic guiding and tracking device for interventional tools, (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. An electromagnetic navigation system for guiding and tracking an interventional tool within an anatomical region, the electromagnetic navigation system comprising:
   a guidewire configured to be inserted into the anatomical region, the guidewire comprising a plurality of guidance electromagnetic sensors configured to generate guidance data that includes (i) at least one of a position and an orientation of the guidewire relative to the anatomical region and (ii) a position of each of the guidance electromagnetic sensors relative to a reference position;
   a hub detachably coupled to the interventional tool, the hub configured to be at least one of translated and rotated relative to the guidewire, the hub comprising a tracking electromagnetic sensor configured to generate tracking data that includes (i) at least one of a position and an orientation of the hub relative to the guidewire and (ii) a position of the tracking electromagnetic sensor relative to the reference position; and
   a navigation controller configured to determine at least one of a position and an orientation of the interventional tool relative to the guidewire based on distance of the position of the tracking electromagnetic sensor of the hub from the position of each of the guidance electromagnetic sensors of the guidewire.

2. The electromagnetic navigation system of claim 1, wherein the plurality of guidance electromagnetic sensors is evenly spaced along the guidewire.

3. The electromagnetic navigation system of claim 1, wherein the plurality of guidance electromagnetic sensors is unevenly distributed between a distal segment and a proximal segment of the guidewire.

4. The electromagnetic navigation system of claim 1, wherein the hub further includes at least one of:
   a radio-opaque marker configured to register the hub,
   an orientation marker configured to visually orient the hub relative to the guidewire,
   a torqueing groove configured to manually orient the hub relative to the guidewire, and
   a locking mechanism configured to clamp the hub onto the guidewire.

5. The electromagnetic navigation system of claim 1, wherein the hub has an annular configuration and the guidewire is configured to extend through the hub.

6. The electromagnetic navigation system of claim 1, wherein the hub is configured to be either adjoinable to a proximal end of the interventional tool or integrated with the proximal end of the interventional tool.

7. The electromagnetic navigation system of claim 6, wherein the navigation controller is further configured to determine the at least one of the position and the orientation of the interventional tool relative to the anatomical region based on a projection of the position of the tracking electromagnetic sensor onto the guidewire.

8. A method for guiding and tracking an interventional tool within an anatomical region, the method comprising:
   inserting a guidewire into the anatomical region, the guidewire including a plurality of guidance electromagnetic sensors;
   at least one of translating and rotating a hub relative to the guidewire, the hub detachably coupled to the interventional tool and including a tracking electromagnetic sensor;
   generating, by the plurality of guidance electromagnetic sensors, guidance data that includes (i) at least one of a position and an orientation of the guidewire relative to the anatomical region and (ii) a position of each of the guidance electromagnetic sensors relative to a reference position;
   generating, by the tracking electromagnetic sensor, tracking data that includes (i) at least one of a position and an orientation of the hub-relative to the guidewire and (ii) a position of the tracking electromagnetic sensor relative to the reference position; and
   determining at least one of a position and an orientation of the interventional tool relative to the guidewire based on distance of the position of the tracking electromagnetic sensor of the hub from the position of each of the guidance electromagnetic sensors of the guidewire.

9. The method of claim 8, wherein the plurality of guidance electromagnetic sensors is evenly spaced along the guidewire.

10. The method of claim 8, wherein the plurality of guidance electromagnetic sensors is unevenly distributed between a distal segment and a proximal segment of the guidewire.

11. The method of claim 8, wherein the hub further includes at least one of:
   a radio-opaque marker configured to register the hub,
   an orientation marker configured to visually orient the hub relative to the guidewire,
   a torqueing groove configured to manually orient the hub relative to the guidewire, and
   a locking mechanism configured to clamp the hub onto the guidewire.

12. The method of claim 8, wherein the hub has an annular configuration and the guidewire is configured to extend through the hub.

13. The method of claim 8, wherein the hub is either adjoinable to a proximal end of the interventional tool or integrated with the proximal end of the interventional tool.

14. The method of claim 8, wherein determination of the at least one of the position and the orientation of the interventional tool relative to the guidewire is further based on a projection of the position of the tracking electromagnetic sensor onto the guidewire.

15. A non-transitory computer-readable storage medium having stored a computer program comprising instructions for guiding and tracking an interventional tool within an anatomical region, the instructions, when the computer program is executed by a computer, cause the computer to:
   receive guidance data that includes at least one of a position and an orientation of the guidewire relative to the anatomical region, the guidance data generated by a plurality of guidance electromagnetic sensors disposed on a guidewire positioned within the anatomical region, the guidance data further including a position of each of the guidance electromagnetic sensors relative to a reference position;
   receive tracking data that includes at least one of a position and an orientation of a hub relative to the guidewire, the tracking data generated by a tracking electromagnetic sensor disposed on the hub that at least one of translates and rotates relative to the guidewire, the tracking data further including a position of the tracking electromagnetic sensor relative to the reference position, wherein the hub is detachably coupled to the interventional tool; and
   determine at least one of a position and an orientation of the interventional tool relative to the guidewire based on distance of the position of the tracking electromagnetic sensor of the hub from the position of each of the guidance electromagnetic sensors of the guidewire.

16. The non-transitory computer-readable storage medium of claim 15, wherein the plurality of guidance electromagnetic sensors is evenly spaced along the guidewire.

17. The non-transitory computer-readable storage medium of claim 15, wherein the plurality of guidance electromagnetic sensors is unevenly distributed between a distal segment and a proximal segment of the guidewire.

18. The non-transitory computer-readable storage medium of claim 15, wherein the hub further includes at least one of:
   a radio-opaque marker configured to register the hub,
   an orientation marker configured to visually orient the hub relative to the guidewire,
   a torqueing groove configured to manually orient the hub relative to the guidewire, and
   a locking mechanism configured to clamp the hub onto the guidewire.

19. The non-transitory computer-readable storage medium of claim 15, wherein the hub has an annular configuration and the guidewire is configured to extend through the hub.

20. The non-transitory computer-readable storage medium of claim 15, wherein determination of the position and the orientation of the interventional tool relative to the guidewire is further based on a projection of the position of the tracking electromagnetic sensor onto the guidewire.

* * * * *